United States Patent [19]
Stallmach et al.

[11] Patent Number: 5,565,775
[45] Date of Patent: Oct. 15, 1996

[54] PRODUCIBLE FLUID VOLUMES IN POROUS MEDIA DETERMINED BY PULSED FIELD GRADIENT NUCLEAR MAGNETIC RESONANCE

[75] Inventors: Frank Stallmach, Leipzig, Germany; Hans Thomann, Bedminster, N.J.

[73] Assignee: Exxon Research and Engineering Company, Florham Park, N.J.

[21] Appl. No.: 494,204

[22] Filed: Jun. 23, 1995

[51] Int. Cl.⁶ ............................................. G01V 3/00
[52] U.S. Cl. ............................................. 324/303; 324/300
[58] Field of Search ............................ 324/300, 303, 324/307, 318, 322, 306

[56] References Cited

U.S. PATENT DOCUMENTS

| | | | |
|---|---|---|---|
| 4,719,423 | 1/1988 | Vinegar et al. | 324/303 |
| 5,278,501 | 1/1994 | Guilfoyle | 324/303 |
| 5,289,124 | 2/1994 | Jerosch-Herold et al. | 324/303 |
| 5,387,865 | 2/1995 | Jerosch-Herold et al. | 324/303 |
| 5,428,291 | 1/1995 | Thomann et al. | 324/303 |

Primary Examiner—Michael Tokar
Attorney, Agent, or Firm—Ronald D. Hantman

[57] ABSTRACT

The present invention is a method to determine the bound and free fluid index of fluids in porous media by pulsed field gradient (PFG) NMR diffusion measurements. The PFG NMR signal is evaluated using a two-fluid model that describes the self diffusion coefficients for the fluid fractions with low and high translational mobilities.

9 Claims, 4 Drawing Sheets

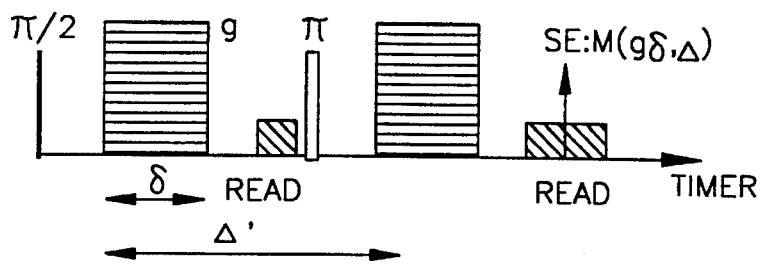
FIG. 1a
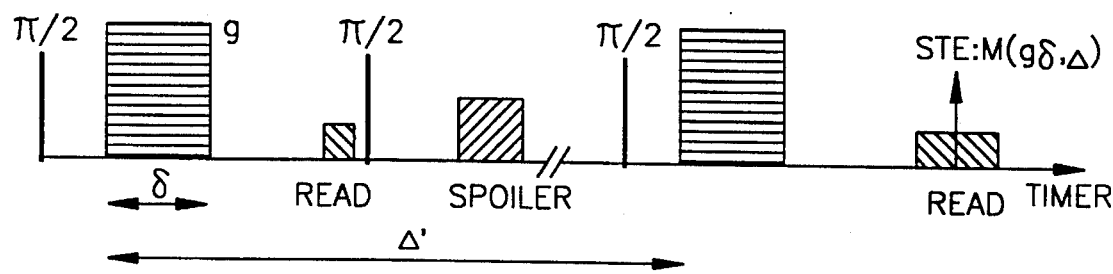
FIG. 1b
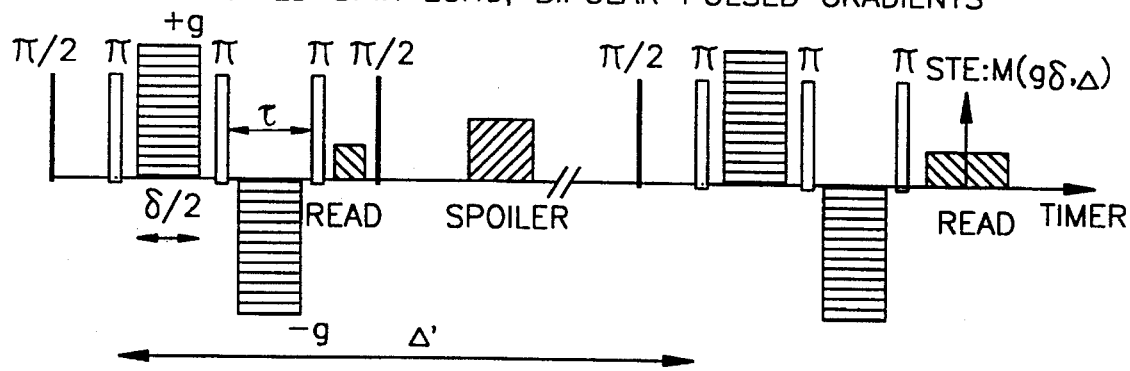
FIG. 1c
 PULSED GRADIENT DIFFUSION ENCODING    READ GRADIENT    SPOILER GRADIENT

— BULK WATER
MARSING SANDSTONE
● HIGH MOBILITY
-○- LOW MOBILITY

MARSING SANDSTONE
● HIGH MOBILITY
-○- LOW MOBILITY

PRODUCIBLE FLUID VOLUMES IN POROUS MEDIA DETERMINED BY PULSED FIELD GRADIENT NUCLEAR MAGNETIC RESONANCE

BACKGROUND OF THE INVENTION

The present invention relates to methods for determining transport properties of fluids in porous media by using nuclear magnetic resonance (NMR) in combination with pulsed magnetic field gradients (PFG). Examples of transport properties include but are not limited to the measurement of the self diffusion coefficients and mean square displacements of the fluid molecules, the relative amounts of fluid molecules having a particular self diffusion coefficient and mean square displacement, respectively and the pore size distribution of the porous medium. In particular the present invention relates to measuring the bound and free fluid volume fractions, also known as the index, of fluids in rocks by measuring the self diffusion coefficients and mean square displacements of both fluid fractions as a function of the observation time and/or the fluid saturation in the pulsed field gradient nuclear magnetic resonance (PFG NMR) experiment.

The free fluid index (FFI) refers to the fluid fraction in a rock pore space, which can be produced under typical reservoir production conditions. The FFI is also sometimes refered to as the "movable" fluid fraction. The bound fluid index (BFI) is the fluid fraction which can not be recovered from the reservoir rock. The petrophysical standard method to determine the FFI and BFI in laboratory measurements on reservoir core plugs is the determination of the capillary pressure curve of the fluid in the pore space by progressive desaturation of the core plug using successively higher rotation speeds of the core plug in a centrifuge. The BFI is the fluid fraction remaining in the pore space of the rock core at a certain capillary pressure i.e. at a certain rotation speed of the centrifuge. The FFI is the fluid fraction which has been removed from the rock core at this rotation speed. Alternatively, the capillary pressure curve and therefore the BFI and FFI can be obtained from mercury injection experiments which also measures the pore size distribution of the rock.

Another approach for determining the BFI and FFI in rocks is the measurement of the transverse ($T_2$) or longitudinal ($T_1$) nuclear magnetic relaxation times of fluids in rocks [see C. Straley et. al. "NMR in Partially Saturated Rocks: Laboratory Insights on Free Fluid Index and Comparison with Borehole Logs", *SPWLA 32nd Annual Logging Symposium*, Jun. 16–19, 1991]. It has been shown that under the condition of the fast diffusion limit, the nuclear magnetic relaxation times of fluids in a single pore depend only on the surface to volume ratio of that pore and is therefore a measure of the pore size [see M. H. Cohen and K. S. Mendelson, "Nuclear Magnetic Relaxation and the Internal Geometry of Sedimentary Rocks", *J. Appl. Phys.* vol. 53, pg. 1127, (1982)]. Since rocks are typically described by a wide range of pore sizes, the observed magnetization decay in the NMR experiment is muli-exponential. The distribution of relaxation times describing this decay is a measure of the pore size distribution in the rock. In this approach, the BFI is the fraction of the fluid having relaxation times less than a certain $T_2$ or $T_1$ cut-off value. These actual cut-off values depend on the effectiveness of the surface relaxation, which is in general, expected to be a function of the detailed properties such as the mineralogy and surface roughness of the rock.

Nuclear magnetic resonance has been used for some time to study fluid flow and diffusion [P. T. Callaghan, *Principles of Nuclear Magnetic Resonance*, Clarendon Press, Oxford 1991]. In general, molecular displacements of fluid molecules can be quantified with NMR by using pulsed magnetic field gradients. With the application of a magnetic field gradient $\vec{G}$, the precession frequency $\omega$ of a nuclear magnetic moment in an external magnetic field $\vec{B}=(0, 0, B_o)$ is a function of the projection of the position $\vec{r}$ of the magnetic moment on the direction of the applied field gradient:

$$\omega = \gamma(B_o + \vec{G} \cdot \vec{r}) \qquad (1)$$

In the PFG NMR experiment the amplitude of the NMR signal, such as a spin echo, is measured as a function of the intensity of applied pulsed magnetic field gradients. Pulse timing diagrams for the applied radio frequency pulses and magnetic field pulses are shown in FIG. 1. The position of each fluid molecule is encoded by the first magnetic field gradient pulse of duration $\delta$ and strength g. After an elapsed time $\Delta$, a second gradient pulse is applied during the refocussing period. The latter is defined by the time period following the second radio frequency pulse in the timing diagram in FIG. 1. The detected signal is the NMR spin echo which is formed at the end of the refocusing period. For stationary spins the phase acquired during the first gradient pulse is reversed by the second pulse which should be matched in intensity $g\delta$. For moving spins the phase reversal is incomplete depending on the distance the molecule has moved during the time between the two gradient pulses. A displacement causes a change in the NMR resonance frequency, or equivalently a change in the phase of the signal, which leads to an attenuation of the observed spin echo amplitude. By repeating the experiment and systematically incrementing the intensity of the matched field gradient pulses one obtains a set of spin echo amplitudes $M(g\delta,\Delta)$ with an attenuation $\psi(g\delta,\Delta)$ which is characteristic for the displacement of the spins. The spin echo attenuation in the PFG NMR is given by [P. T. Callaghan, *Principles of Nuclear Magnetic Resonance*, Clarendon Press, Oxford 1991]:

$$\psi(g\delta,\Delta) = \frac{M(g\delta,\Delta)}{M(0,\Delta)} = \int p(\vec{r}) \int P(\vec{r}|\vec{r'},\Delta) \exp[i\gamma\vec{\delta g}(\vec{r'}-\vec{r})] d\vec{r'} d\vec{r} \qquad (2)$$

where $P(\vec{r}|\vec{r'}, \Delta)d\vec{r'}$ denotes the conditional probability (propagator) of finding a molecule initially at position $\vec{r}$, after a time $\Delta$ in the volume element $d\vec{r'}$ at $\vec{r'}$ and $p(\vec{r})$ is the initial spin density. In a homogeneous medium, the propagator $P(\vec{r}|\vec{r'},\Delta)$ is a Gausian function of the displacement $(\vec{r'}-\vec{r})$. Therefore, the spin echo attenuation becomes a exponential function of the square of the intensity of the applied field gradient pulses with the self diffusion coefficient D as decay rate:

$$\psi(g\delta,\Delta) = \exp[-(\gamma\delta g)^2 D\Delta] \qquad (3)$$

For self-diffusion in restricted geometries it has been shown that deviations from the pattern predicted by eq. [3] occur at high intensities of the applied field gradients where the spin echo amplitude has already been attenuated by 2–3 orders of magnitude [P. T. Callaghan et. al., *Nature*, 351,467 (1991)]. With increasing observation time these effects become more pronounced since more molecules will experience restrictions of their translational motion due to the pore walls. The pore geometry and a measure of the pore sizes can be estimated from this non-exponential spin echo attenuation [see for example, P. S. Sen and M. D. Hurlimann, *J. Chem Phys.*, 101, 5423 (1994). However, at small $(\gamma \delta g)^2$ eq. [3] may still be applied yielding a observation time dependent apparent self diffusion coefficient D, which contains information on pore sizes of the porous medium.

The present invention provides a method for obtaining at least one transport property of fluids in porous media by encoding the self diffusion of the fluid molecules in the pore space by PFG NMR.

In one embodiment of the present invention, the time dependence of the mean square displacements of the fluid molecules are obtained, which show that a fraction of the molecules experiences a highly restricted self diffusion (low translational mobility) during the time scale of the PFG NMR experiment while the other fraction shows a high translational mobility with only slight deviations from the self diffusion coefficient of the bulk fluid. The ratio of the fluid with low translational mobility to the overall fluid is shown to be the BFI. The pore size of the rock as seen by both fluid fractions may be estimated from the time dependence of the mean square displacements.

SUMMARY OF THE INVENTION

The present invention is a method for obtaining at least one fluid transport property of a porous material. The steps of the method include obtaining a porous material with a variable amount of fluid in the pore space, applying radio frequency pulses leading to a coherent precession of the nuclear spins for a preselected species of nuclear spins on molecules in the fluid, applying magnetic field gradients to encode the displacement of fluid molecules during a time interval, repeating the application of the radio frequency and magnetic field gradient pulses for different values of the magentic field gradient intensities, recording the nuclear magnetic resonance (NMR) signal for each magnetic field gradient intensity, and determining the fluid transport property from the NMR signal. In a preferred embodiment, the transport property is the bound fluid volume which is also known as the bound fluid index.

BRIEF DESCRIPTION OF THE DRAWINGS

FIG. 1: Pulsed field gradient NMR timing diagram for diffusion (and flow) encoding. The spin echo amplitude is measured as function of the pulsed field gradient intensity $g\delta$. (a) shows a simple version using the primary spin echo. (b) shows a version using the stimulated spin echo. This sequence is useful to increase the observation time $\Delta$ for systems where $T_2 \leq T_1$. (c) is a variation of (b) which includes $\pi$ pulses and reversal of the gradient polarity to reduce the effects of internal magnetic field gradients [see R. M. Cotts et al., "Pulsed Field Gradient Stimulated Echo Methods for Improved NMR Diffusion Measurements in Heterogeneous Systems", *J. Magn. Reson.*, vol. 83, 252 (1989)]. Internal magnetic field gradients are often encountered when heterogeneous media such as rocks are placed in a magnetic field. Read and spoiler gradients may be added in these sequences. Read gradients are used for the encoding of spatial information and/or for assisting the matching of the pulsed field gradient intensities if the read gradient is parallel to the pulsed gradient.

DESCRIPTION OF THE PREFERRED EMBODIMENT

Figure 2:
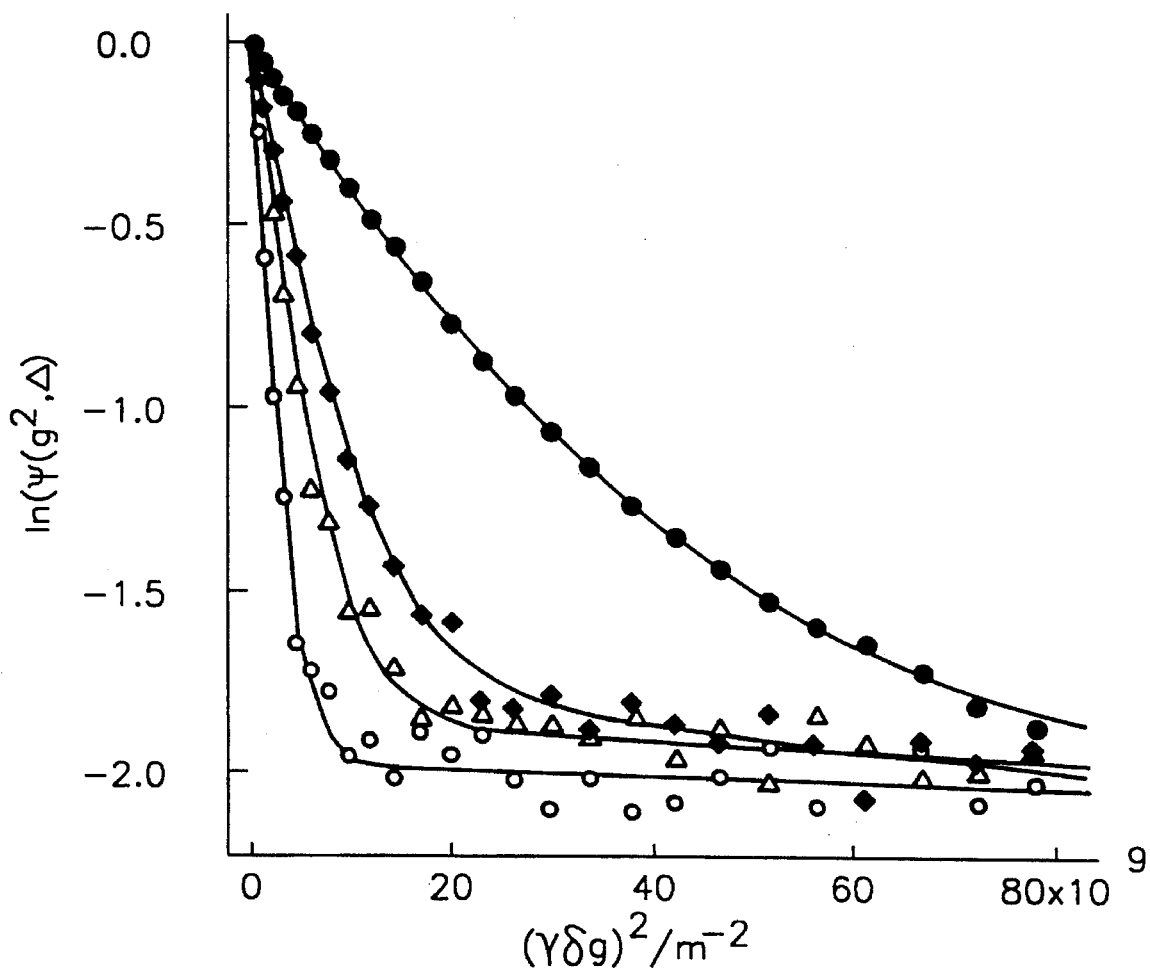
FIG. 2 shows the spin echo attenuations $\psi(g\delta,\Delta)$ as a function of the square of the applied pulsed field gradient intensity $(g\delta)^2$ at different observation times $\Delta$ for 100% water saturation for a marsing sandstone. The solid lines represent the fitting of the experimental data to the Two-Fluid-Model.

In the PFG NMR the translational motion of the molecules is encoded with pulsed field gradients. Using the Einstein relation for Brownian motion, the mean square displacement $(r^2(\Delta))$ of the fluid molecule can be determined from the observation time dependence of the self diffusion coefficient $D(\Delta)$ defined according to eq. 3. In an isotropic medium:

$$(r^2(\Delta))=6D(\Delta)\Delta \quad (4)$$

$D(\Delta)$ is equal to the bulk diffusion coefficient of the fluid if the self diffusion is unrestricted. Eq. [3] holds only if all molecules of the fluid carrying the nuclear spin under investigation have the same characteristics in their translational mobility. Necessary (but not necessarily sufficient) conditions for this to be true are that the fluid is comprised of only one chemical type and in one physical state and that all molecules experience the same restriction of their diffusion path due to collisions with the pore wall. If there are several populations of the same fluid molecule in the pore space which are distinguishable by their mean square displacements during the time scale of the PFG NMR experiment, the spin echo amplitude and consequently the spin echo attenuation consists of a superposition of exponential functions of the form of eq. [3] [see J. Kaerger, H. Pfeifer, W. Heink, *Advances in Magnetic Resonance*, 12, 1 (1988)]. For two distinguishable fluid components, the spin echo attenuation can be described by:

$$\psi(g\delta,\Delta)=p_h exp[-(\gamma\delta g)^2 D_h \Delta]+p_l exp[-(\gamma\delta g)^2 D_l \Delta] \quad (5)$$

$$1=p_h+p_l \quad (6)$$

where $p_{h(l)}$ denotes the fluid fraction having the self diffusion coefficient $D_{h(l)}$. The indexes h and l refer to the fluid molecules with high and low translational mobilities respectively. Using eq. [4], the corresponding mean square displacements $(r^2(\Delta))_{h(l)}$ for both fluid fractions are obtained. The time dependence of $(r^2(\Delta))_{h(l)}$ is used to identify the characteristics of the fluid transport through the pore space. If the mean square displacement of the fluid with the low translational mobility is independent of the observation time $((r^2(\Delta))_l=(r^2)_l)$, the diffusion of this fluid fraction is highly restricted in the pore space. The mean square displacement is limited by the maximum size of the pores containing that fluid fraction. It may be used to estimate an upper limit of the pore radius $R_{low}$ entered by fluid having a low translational mobility:

$$R_{low}^2 \leq \langle r^2 \rangle_l \quad (7)$$

For self diffusion in a sphere with radius $R_{sphere}$:

$$R_{sphere}^2 = \frac{5}{6} \langle r^2(\Delta = \infty) \rangle_l \quad (8)$$

The capillary pressure $p_c$ for fluid in a pore of radius R is estimated by the Young-Laplace equation:

$$p_c = \frac{2\gamma \cos\theta}{R} \quad (9)$$

where $\gamma$ is the air/fluid interfacial tension and $\theta$ is the contact angle between fluid and air at the pore surface. Therefore, the minimum pressure $p_{min}$ required to move the fluid with low translational mobility out of the pores by centrifugation of the rock sample is given by:

$$p_{min} = \frac{2\gamma \cos\theta}{R_{low}} \geq \frac{2\gamma \cos\theta}{\langle r^2 \rangle_l^{0.5}} \quad (10)$$

In rock samples, $R_{low}$ is usually on the order of a few microns. Consequently, for a wetting fluid (e.g. $\theta$=0.25 $\pi$, $\gamma$=60 dyne/cm) $p_{min}$ is typically on the order of 50 to 100 psi. This range of values corresponds reasonably well to the cut-off capillary pressure used to determine the bound fluid fraction (BFI) in rocks by centrifugation of the sample. Since the relative, amount of fluid with low translational mobility $p_l$ measured by PFG NMR and the BFI obtained by centrifugation of the rock sample measure the fluid fraction in small pores, we can make the following associations:

$$BFI = p_l \text{ and } FFI = p_h \quad (11)$$

For small observation times the mean square displacement of the fluid with high translational mobility $(r^2(\Delta))_h$ is expected to coincide with the corresponding value of the bulk fluid. Only at sufficient long observation times $\Delta > \Delta_R$ do a substantial part of these molecules experience restrictions of their diffusion path due to collisions with the pore wall. At observation times above $\Delta_R$, $(r^2(\Delta_R))_h$ clearly deviates from of the mean square displacement $(r^2(\Delta))_{bulk}$ of the bulk fluid. Consequently, the root mean square displacement of the fluid at $\Delta_R$ represents an estimate for the minimum radius $R_{high}$ of the pores containing the fluid with high translational mobility:

$$R_{high}^2 \approx (r^2(\Delta_R))_h \quad (12)$$

$R_{high}$ may be considered as the lower limit of the mean free diffusion path of the fluid molecules with high translational mobility until they bounce against the pore wall.

IMPLEMENTATION

Application of the Two-Fluid-Model for PFG NMR Self Diffusion Studies of Fluids in Rocks Diffusion (and flow) measurements with the PFG NMR technique are performed by generation of a primary or stimulated spin echo using an appropriate rf pulse sequence (a combination of $\pi/2$ and $\pi$ pulses) and simultaneous application of at least two pulsed magnetic field gradients of separation $\Delta'$ for diffusion encoding. Examples for pulse sequences are given in FIG. 1. FIG. 1c is an example for a pulse sequence suitable for measuring diffusion of fluids in the presents of internal magnetic field gradients caused by susceptibility differences between the fluid and grain material in a porous medium. The $\pi$ rf pulses in this sequence constantly refocus phase shifts of the nuclear magnetic moments due to internal magnetic field gradients but allow the co-addition of phase shifts due to pulsed magnetic field gradients of opposite polarity $\pm g$. Therefore, the effect of diffusion of the fluid molecules in internal magnetic field gradients on the spin echo attenuation is canceled [R. M. Colts, M. J. R. Hoch, T. Sun and J. T. Markert, *Journal of Magnetic Resonance*, 83, 252–266 (1989)]. Due to the finite duration $\delta$ of the pulsed magnetic field gradients, the observation time $\Delta$ entering into eqs. [2–5,] is related to their separation $\Delta'$ by $$\Delta = \Delta' - \frac{\delta}{3} - \frac{\tau}{2} \quad (13)$$

were $\tau$ is equal to zero in the sequences a) and b ). A number of variations of the PFG NMR pulse sequences shown in FIG. 1 have also been described by Cotts for measuring the fluid self diffusion in heterogeneos systams.

For PFG NMR diffusion measurements of fluids in rocks (or other porous materials) in a laboratory NMR spectrometer, rock sample cores of typically 1 cm diameter and 2 cm length are used. However, their size is limited only by the excitation volume of the rf coil and the volume in which constant field gradients are generated by the gradient coil system. The samples must be filled with fluid using an appropriate procedure (e.g. pressure saturation or imbibing of the fluid by an evacuated sample) with the desired fluid. To prevent the loss of fluid during the NMR measurements, the fluid saturated rock samples must be coated or sealed. It is beneficial for the interpretation of the measurements that the material used for coating or sealing does not exhibit an NMR spin echo signal using the PEG NMR sequence selected for the diffusion measurement of the fluid in the sample. As example, for $^1H$ PFG NMR measurements of water self diffusion in rocks the samples might be sealed by Teflon tape since it does not contain hydrogen (H) or by a layer of epoxy which usually does not show a stimulated or primary spin echo at observation times exceeding a few $10^{-3}$ seconds.

An example of the results for the PFG NMR diffusion measurements with water in rocks is given in FIG. 2. It shows the spin echo attenuations $\psi(g\delta,\Delta)$ as a function of the square of the applied pulsed field gradient intensity $(g\delta)^2$ for a fully saturated marsing sandstone (porosity $\phi$=23.9%, air permeability k=1276 md). The pulse sequence used is given in FIG. 1c. The parameters were $\delta$=1.41 ms, $\tau$=1.81 ms and the observation time $\Delta$ was changed between 25 ms and 600 ms. The pulsed field gradient strength $\pm g$ was lineary increased up to $g_{max}$=0.8 T/m, and for each value of g the amplitude of the spin echo was measured in the presence of a small read gradient of about 2 mT/m pointing parallel to g. The read gradient was used to assist the matching of the intensities $(g\delta)$ of the succeeding pairs of bipolar field gradient pulses [see e.g F. Stalhnach, J. Kaerger and H. Peifer. *Journal of Magnetic Resonance*, A102, 270 (1993)].

Figure 3A:
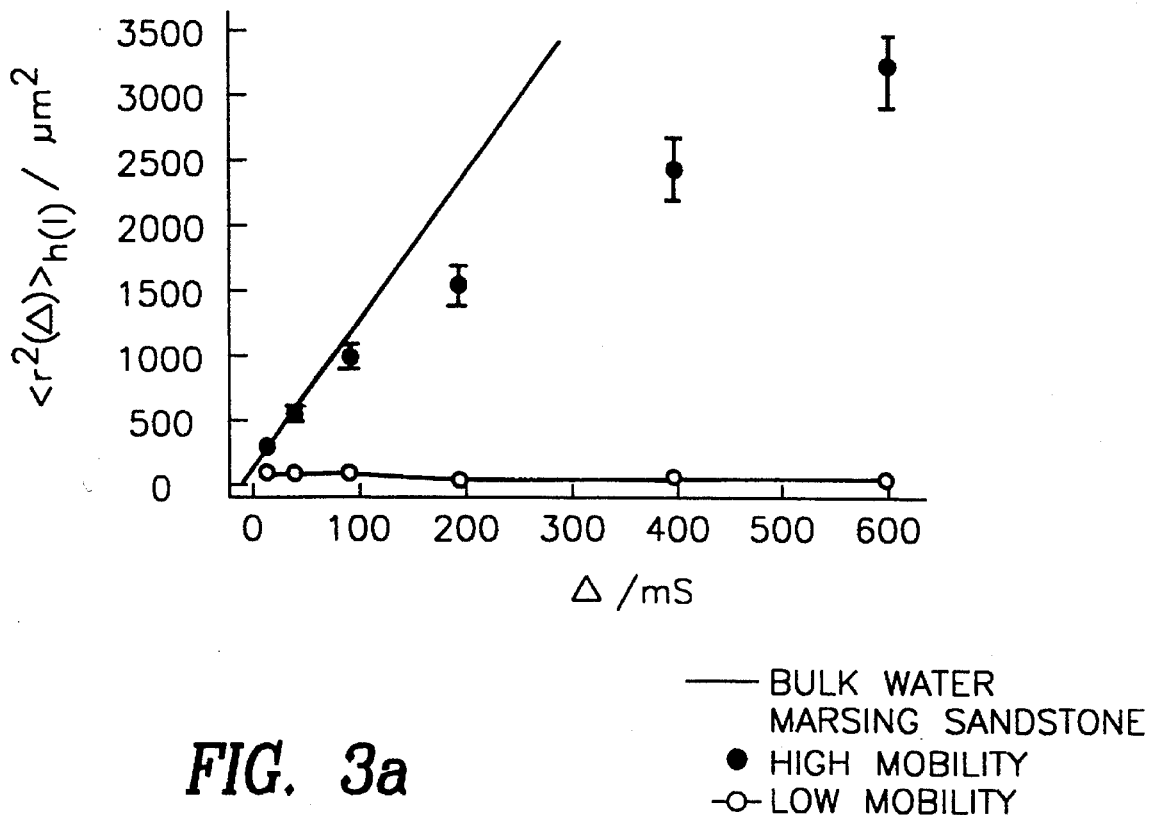
FIG. 3a) shows the observation time dependence of the mean square displacements of water with high and low translational mobilities, respectively in the marsing sandstone. The solid line represents the time dependence of the mean square displacement of bulk water. b) represents the observation time dependence of both fluid fractions in this sandstones. a) and b) are obtained by fitting the Two-Fluid-Model (eq. [5]) to experimental data as given in FIG. 2.

In contrast to bulk water, the spin echo attenuation for water in sandstone rocks is found to be non-exponential with $(g\delta)^2$. However, as shown by the solid lines in FIG. 2 the experimental data points can be well represented by the double-exponential function given in eq. [5]. The fit of this so called "Two-Fluid Model" to the experimental spin echo attenuation yields the self diffusion coefficients $D_{h(l)}$ and the fractions $p_{h(l)}$ of water molecules with high and low translational mobility, respectively. According to eq. [4], the observation time dependence of the mean square displacement for both fluid fractions may be calculated. The results for water in the marsing sandstone are shown in FIG. 3a. For comparison the time dependence of the mean square displacement of bulk water is also shown in the figure. The mean square displacement of water with high translational mobility $(r^2(\Delta))_h$ is found to increase over the whole observation time range. However, this increase is non-linear and slower than for bulk water. Clear deviations from the mobility of bulk water occur for observation times $\Delta > 50$ ms which means that in this rock, most of the water molecules with high translational mobility experience restriction of their diffusion path due to collisions with the pore wall only after a diffusion time of about 50 ms. This corresponds to root mean square displacements $(r^2(\Delta_R=50\ ms))_h^{0.5}$ of about 25 µm. Consequently, according to eq. [12] the minimum radius $R_{high}$ of the pores containing the fluid with high translational mobility is 25 µm.

The mean square displacement of water with low translational mobility $(r^2)_l$ in the marsing sandstone is on the order of 20 µm². In particular, it does not increase with increasing observation time. This is evidence for restricted diffusion and likely originates from fluid in small pores. According to eq. [7], the pore radius $R_{low}$ as seen by the water molecules with low translational mobility is less than 5 µm.

Figure 3B:
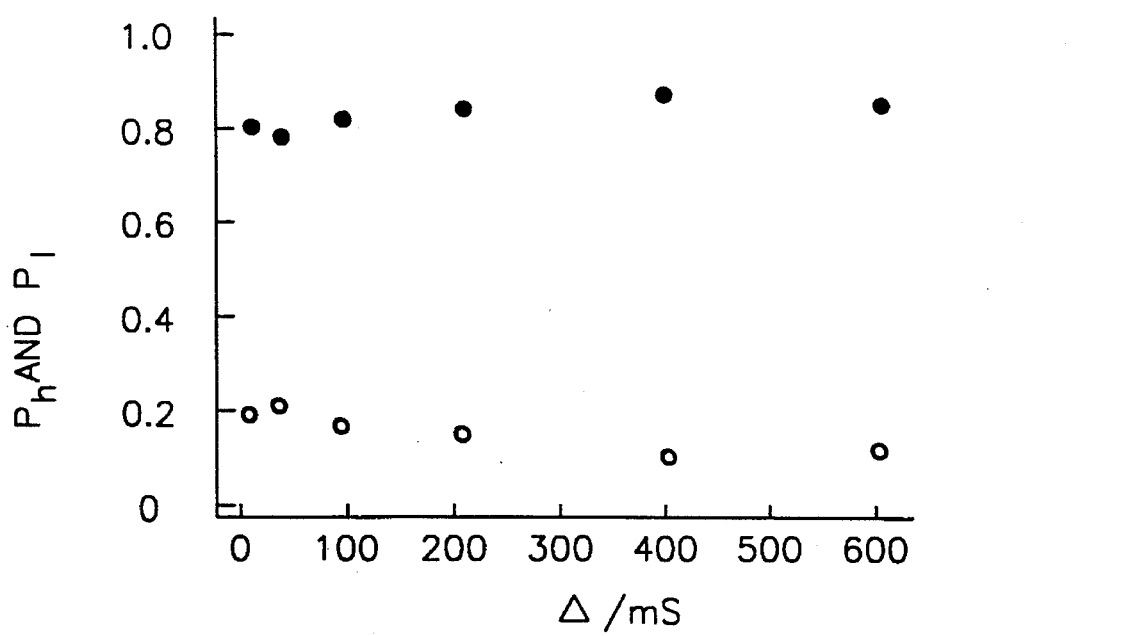

The fluid fractions $p_l$ and $p_h$ are plotted in FIG. 3b as function of the observation time. $p_l$ is roughly 0.21 (or 21%) at short $\Delta$ and decreases only slightly longer observation times. Since the nuclear magnetic relaxation in small pores is more effective than in large pores, the relative contribution of small pores to the spin echo amplitude decreases with increasing observation time. This effect is called "relaxation weighting" and has to be taken into account for the calculation of BFI and FFI from PFG NMR diffusion data, if strong observation time dependencies of $p_l$ and $p_h$ are observed. The relaxation weighting is negligible for the marsing sandstone, and according to eq. [11], the BFI as predicted from PFG NMR diffusion measurements and application of the Two-Fluid-Model is expected to be about 21%.

Table 1 shows a comparison of the B FI determined by two NMR methods and for comparison a standard core analysis procedure. One NMR method used was based on the multi-exponential analysis of the transverse magnetization decay measured using the CPMG technique [see M. N. Miller et al., "Spin Echo Magnetic Resonance Logging: Porosity and Free Fluid Index Determination", paper SPE 20561 presented at the 65th Annual Technical Conference and Exhibition of the Society of Petroleum Engineers, New Orleans, La., Sep. 23–26, 1990; also, R. L. Kleinberg et al., "Nuclear Magnetic Resonance of Rocks: T1 vs. T2", paper SPE 26470 presented at the 65th Annual Technical Conference and Exhibition of the Society of Petroleum Engineers,

TABLE 1

Bond fluid index (BFI) as a % of total porosity determined by different methods for water in sandstone rocks

| | Rock Properties | | BFI in % by | | |
|---|---|---|---|---|---|
| type | porosity % | permeability md | CPMG NMR 30 ms $T_2$ | PFG NMR pl | CAP PRE 50 psi |
| silver | 30.2 | 21,000 | 19 | 6 | 6 |
| marsing | 23.9 | 1,276 | 33 | 21 | 11, 19‡ |
| red navajo | 23.6 | 1,138 | 21 | 5 | 6 |

‡results for different core plugs

Houston, Tex., Oct. 3–6, 1993]. The PFG NMR BFI data in Table 1 is determined using the new Two Fluid Model analysis of the PFG NMR data. These NMR methods for determining the BFI are compared to the petrophysical standard method of measuring the residual water saturation at 50 psi capillary pressure (CAP PRE). The fluid fraction of low translational mobility as obtained by applying the proposed Two-Fluid-Model to PFG NMR self diffusion measurements of tfluids in rocks is found to be in good agreement with the bond fluid index (or "non-producable" fluid fraction) from the petrophysical standard method. These results confirm the validity of the assumtions leading to eq.[11].

PFG NMR diffusion measurements may also be performed if the porous material is only partially saturated with a fluid or if more than one type of fluid occupies the pore space (e.g. oil and water). In the case that more than one type of fluid occupies the pore space, if molecules of each fluid type contributes to the observed PFG NMR signal, the signal observed is then a superposition of the NMR signals from the individual components. The spin echo amplitude is than given by:

$$M(g\delta,\Delta) = \sum_{i=1}^{n} m_i\{p_{hi}\exp[-(\gamma\delta g)^2 D_{hi}\Delta] + p_{li}\exp[-(\gamma\delta g)^2 D_{li}\Delta]\} \quad (14)$$

$$1 = p_{hi} + p_{li} \quad (15)$$

where $m_i$ is the overall contribution of the $i^{th}$ fluid component to the spin echo amplitude (proportional to the number of those fluid molecules), and $p_{li(hi)}$ and $D_{li(hi)}$ denote the fractions and the self diffusion coefficients of fluid with low and high translational mobility of the $i^{th}$ fluid component, respectively. To simplify the multiexponential analysis of the spin echo decay in multi-component systems, NMR techniques for signal separations can be employed. Commonly used methods are:

(i) Fourier transformation of the spin echo signal recorded in the time domain if the different fluid components contain the same nuclei under investigation but have different chemical shifts so that their NMR signals in the frequency domain appear at different Larmor frequencies. The attenuation of each individual frequency component with increasing field gradient intensity may then be analyzed according to eq. [11].

(ii) Selective excitation of a part of the fluid components by using shaped rf pulses. This technique requires also that the individual fluid components are distinguishable by their chemical shifts. A spin echo is only obtained from the excited components of all fluid molecules.

(iii) Using labeled isotopes in fluid mixtures. The diffusion of labeled isotopes of fluid molecules may be observed without interference from all other fluid components if the considered component only contains the NMR isotope under investigation. As an example, in a mixture of water and oil, the oil diffusion can be observed by $^1H$ PFG NMR without the superposition from water NMR signal, if deuterated water is used.

Figure 4:
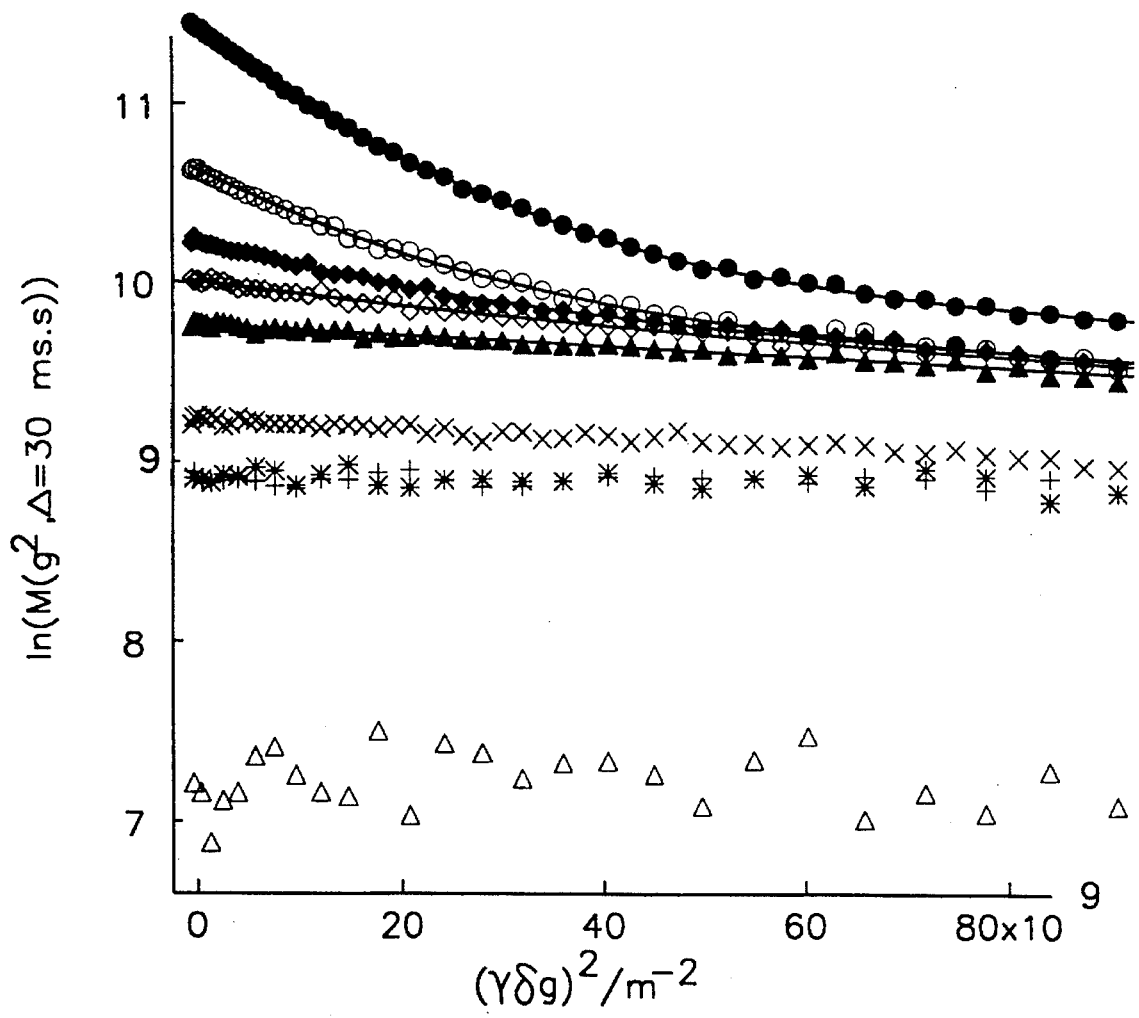
FIG. 4 shows the spin echo amplitude $M(g\delta,\Delta)$ as a function of the square of the applied pulsed field gradient intensity $(g\delta)^2$ at 30 ms observation time for different water saturation s in the same marsing sandstone. The solid lines represent the fitting of the experimental data by the Two-Fluid-Model for the partially saturated rock according to (eq. [14]).

PEG NMR self diffusion measurements described here may also be applied to porous samples in which the pore space is only partially occupied by fluids. Data for a rock at different water saturations s are shown in FIG. 4. With decreasing water saturation the signal amplitude at $(g\delta)^2=0$ decreases corresponding to a decreasing number of fluid molecules in the pore space of the rock. In the range from 100% to about 32% water saturation, the fast decaying component of the signal amplitude disapears in the signal attenuation indicating, that the water with high translational mobility is removed from the pore space. For saturations below 32% only a simple exponential spin echo attenuation has been observed and for saturations below 24% the no decay of the spin echo amplitude with the intensity of the applied pulsed field gradients was observed.

What is claimed is:

1. A method for obtaining at least one fluid transport property of a porous material comprising:
   (a) obtaining a porous material with a variable amount of fluid in the pore space;
   (b) applying radio frequency pulses leading to a coherent precession of the nuclear fluid spins for a preselected species of nuclear spins on molecules in the fluid;
   (c) applying magnetic field gradients to encode the displacement of fluid molecules during a time interval;
   (d) repeating step (c) for different values of magnetic field gradient intensities;
   (e) recording the NMR signal in step (d) for each magnet field gradient intensity;
   (f) determining said fluid transport property from said NMR signal.

2. The method of claim 1 wherein said transport property is the bound fluid index.

3. The method of claim 1 wherein the said method is repeated for a different time intervals.

4. The method of claim 3 and wherein said transport proper is the bound fluid index.

5. The method of claim 1 wherein said variable amount of fluid varies from 5% to 100%.

6. The method of claim 3 wherein said fluid varies from 5% to 100% depending on the type of porous material.

7. The method of claim 1 wherein said porous material with said variable amount of fluid is obtained by inserting said fluid into said material.

8. The method of claim 1 wherein said porous material with said variable amount of fluid is obtained in its natural state.

9. The method of claim 1 wherein said fluid includes more than one type of fluid.

* * * * *